United States Patent [19]

Popiel et al.

[11] Patent Number: 5,183,950
[45] Date of Patent: Feb. 2, 1993

[54] COMMERCIAL STORAGE AND SHIPMENT OF ENTOMOGENOUS NEMATODES

[75] Inventors: Irene Popiel, Mountain View; Karen D. Holtemann, San Jose, both of Calif.; Itamar Glazer, Bet Dagon, Israel; Christopher Womersley, Honolulu, Hi.

[73] Assignee: Biosys, Palo Alto, Calif.

[21] Appl. No.: 101,530

[22] Filed: Sep. 28, 1987

Related U.S. Application Data

[63] Continuation-in-part of Ser. No. 897,660, Aug. 18, 1986, abandoned.

[51] Int. Cl.$^5$ .................... C12N 5/18; A01K 67/00; A01N 25/34
[52] U.S. Cl. .................... 800/2; 119/6.7; 424/405; 424/408
[58] Field of Search .................... 119/1, 6.7, 6.5, 6.6; 800/1; 424/408, 402

[56] References Cited

U.S. PATENT DOCUMENTS

| | | | |
|---|---|---|---|
| 3,271,243 | 9/1966 | Cords et al. | 424/93 |
| 3,654,903 | 4/1972 | Montgomery | 119/15 |
| 4,178,366 | 12/1979 | Bedding | 424/93 |
| 4,334,498 | 6/1982 | Bedding | 119/1 |
| 4,417,545 | 11/1983 | Finney | 119/1 |
| 4,615,883 | 10/1986 | Nelsen et al. | 424/93 |

FOREIGN PATENT DOCUMENTS

| | | | |
|---|---|---|---|
| 8100037 | 1/1981 | PCT Int'l Appl. | |
| 8503412 | 8/1985 | PCT Int'l Appl. | 119/1 |
| 8601074 | 2/1986 | PCT Int'l Appl. | 119/1 |
| 2174907 | 11/1986 | United Kingdom | |

OTHER PUBLICATIONS

Crowe et al., editor and author, "Dry Biological Systems" Academic Press, Inc., publisher, (1978) pp. 23–51.
Crowe et al., editor, "Dry Biological Systems" Academic Press, Inc., publisher, (1978) pp. 155–173.
Crowe et al., J. Exp. Zool. (1975) 193:323–334.
Demeure et al., "Plant Parasitic Nematodes" (1981) Academic Press, New York, pp. 205–226.
Demeure et al., J. Nematol. (1979) 11:189–195.
Bedding, Appl. Biol. (1984) 104:117–120.
Crowe et al., J. Exp. Zool. (1979) 207:431–437.
Dutky et al., J. Insect Pathol. (1964) 6:417–422.
Evans et al., "Nematodes as Biological Models" (1980).
Freckman et al., "New Trends in Soil Biology" (Lebrun, editor) 1983 University Catholique de Louvain Press, pp. 395–403.
Hara et al., U.S. Dept. Agric. Sci. Ed. Admin. Advs. Agric. Technol. (Jun. 1981) pp. 1–8.
Howell, J. Invert. Path. (1979) 33:155–158.
Kamionek et al., "Eleventh International Sym. Nematol." European Soc. Nematol. (1972).
Lindegren et al., U.S. Dept. Agric. Sci. Ed. Admin. Advs. Agric. Technol. (Feb. 19, 1979) pp. 1–5.
Madin et al., J. Exp. Zool. (1975) 193:335–342.
Poinar, "The Natural History of Nematodes" (1983) Prentice Hall, Inc. New Jersey, pp. 161–200.
Simons et al., J. Invertebrate Pathol. (1973) 22:228–230.
Womersley, Comp. Biochem. Phys. (1981) 70B:669–678.
Womersley, Biological Abstracts (1981) 72(11):7619.
Womersley, Comp. Biochem. Physiol. (1981) 68A:2-49–252.
Demeure et al., Revue. Nematol. (1979) 2(2):203–210.
Glaser, J. Exp. Zool. (1940) 84(1):1–12.
Glazer et al., Biol. Abstr. 77(8):6594 reference No. 59926.
Poinar et al., Ent. Scand. (1971) 2(4):301–303.
Robinson et al., Biol. Abstr. 78(3):2270 reference No. 19993.
Womersley, Vistas on Nematology Twenty-Fifth Anniversary of the Society of Nematologists, Inc., Maryland, pp. 165–173.
Robinson et al. 1984. J. Nematol. 6, 86–91.

Primary Examiner—Elizabeth C. Weimar
Assistant Examiner—Christopher Low
Attorney, Agent, or Firm—Morrison & Foerster

[57] ABSTRACT

Methods and materials for inducing anhydrobiosis in entomogenous nematode infective juveniles and then maintaining and storing them in an apparently anhydrobiotic state are described. Infective juveniles are induced into an anhydrobiotic state at relatively high relative humidity prior to optional lowering of the ambient relative humidity for storage and shipment. Suitable containers are also disclosed.

4 Claims, 2 Drawing Sheets

COMMERCIAL STORAGE AND SHIPMENT OF ENTOMOGENOUS NEMATODES

This is a continuation-in-part of U.S. Ser. No. 897,660, filed Aug. 18, 1986, now abandoned.

TECHNICAL FIELD

The invention relates to insect control employing biological agents especially for the benefit of agriculture, garden and household insects. In particular, it relates to methods to desiccate, package, store, and ship insect parasitic nematodes in both large and small quantities while maintaining their viability and pathogenicity to insects.

BACKGROUND ART

Nematodes represent a group of unsegmented round worms. They are simple in anatomy, having a simple gut and elongated fusiform shape. They are divided into numerous Families, some which are free living while others are parasitic to plants or animals. Those which are parasitic to insects are called entomogenous or entomopathogenic nematodes.

The Order of greatest commercial interest for insect control is the Order Rhabditida, which contains several Families, many of whose members are parasitic to insects. Prominant among these Families are the Steinernematids and Heterorhabditids. A general discussion of the classification of nematodes, and the entomogenous Families thereof is found in Poinar, G.O., "The Natural History of Nematodes" (1983), Prentice-Hall, Inc., N.J.

Nematodes have a standard life cycle comprising five stages which are delineated by a molting process in which a new cuticle is formed and the old one shed. Briefly, the adults of stage 5 reproduce, and the eggs generate stage 1 larvae, which, under appropriate conditions, transit to stage 2. Normally, the stage 2 larvae simply develop to stage 3 larvae and thence to stage 4 larvae, which then complete the cycle to the adult stage. However, and of interest to the use of nematodes for insect control, when conditions are relatively unfavorable for continuing growth and reproduction, the stage 2 larvae of Steinernematid and Heterorhabditid nematodes develop instead into "stage 3 infective juveniles" or "IJs". Under these conditions, the cuticle characteristic of the second stage is retained and is called the sheath. It completely encloses the nematode. IJs are infective to insects and complete their life cycle through stage 4 and adult at the expense of the host.

Steinernematid and Heterorhabditid IJ nematodes are an effective means of insect control. They are identifiable morphologically and normally live in surface water films around soil particles. They require oxygen and moisture for survival, but do not feed; they utilize their own food reserves as an energy source. They remain infective if the sheath is removed.

One other aspect of Steinernematid and Heterorhabditid nematode biology is significant: nematodes within these families are symbiotic with species of bacteria which are primarily but not totally responsible for their entomopathogenic properties.

The commercial production of Steinernematid and Heterorhabditid nematodes and their use in insect pest control presents a number of challenges which have only recently begun to be met. Large scale production of IJs has been developed at a number of locations, and a number of techniques have been tried. See, for example, Soviet Patent 726,164; Apr. 8, 1980; PCT Patent Application No. 86/01074 published Feb. 27, 1986; U.S. Pat. No. 4,334,498 and U.S. Pat. No. 4,178,366.

Formulations have also been devised for the application of infective juveniles to the soil. See, for example, Soviet Patent Application No. 378,222 and U.S. patent application Ser. No. 4,178,366. One approach utilizes a suspension in light mineral oil. In addition, Japanese Patent Application No. 60/260,678 proposes a fermented compost support for the application of the nematodes.

An additional and serious problem in commercialization of insect control using Steinernematid and Heterorhabditid nematodes arises in the large scale shipment and storage of the infective juveniles in a state which maintains their viability and pathogenicity. Heretofore, relatively impractical methods, which only minimally reduce nematode metabolism have been used. These include storage and transportation in oxygenated water (Dutky, S. R., et al, *J Insect Pathol* (1964) 6:417–422) in sterile water or 0.1% formalin in flasks (Poinar, G. O., "Nematodes for Biological Control of Insects" (1975) CRC Press, Boca Raton, Fla.) or in 0.1% formalin on moist polyurethane sponge or saturated filter paper (Bedding, R.A. *Ann Applied Biol* (1984) 104:117–120; Hara, A. H. et al, *USDA Adv Agric Technol* W-16 (1981); Howell, J. F., *J Invert Pathol* (1979) 33:155–156 and Lindergren, J. E. at al, *USDA Adv Agric Technol* W-3 (1979)). Other shipment and storage techniques have included the use of wood chips and activated charcoal.

Recently, additional approaches have been disclosed. U.S. Pat. No. 4,417,545 describes a shipping and/or storage container for nematodes and/or their eggs in their dormant state. This container basically sandwiches the nematodes and eggs between two pieces of foam which are saturated with water and thus maintain a high level of humidity. This approach is however directed to the noninfective stages of the worm and does not relate to the shipment of infective juveniles. PCT Application WO85/03412 suggests methods of transport and storage which depend on maintaining putative anaerobic conditions and the presence of an antimicrobial agent. High osmotic strength solutions are also used to prevent bacterial growth. The proposed storage conditions also include an adsorbent such as charcoal or synthetic resins, although it is not clear what these agents are expected to adsorb. The disclosure exemplifies the use of formaldehyde as an antimicrobial, and proposes storage containers which contain both the nematodes and adsorbent charcoal.

The approach of the present invention is to maintain the infective juveniles of the Steinernematid and Heterorhabditid nematodes in a state of dormancy so that their food reserves are not used up, and so that upon return to suitable conditions they revive and remain pathogenic to the insect host. In short, the methods and containers disclosed in connection with the present invention are designed to maintain the infective juveniles in a "cryptobiotic" state—a state of dormancy in which metabolism is suppressed. Several ways of doing this, with varying degrees of success, are known for organisms in general. The most generally suggested method and perhaps the most universally applicable is the induction of cryobiosis, i.e., reduced metabolism at low, usually freezing temperatures. In addition, and more difficult to achieve, are anhydrobiosis, which is induced by evaporative desiccation and the closely related osmobiosis, which is induced by osmotic desiccation.

There is an extensive literature on anhydrobiosis in nematodes in general, although any detailed disclosure related to the nematodes of interest in insect control is limited to a single report (Simons, W. R., and Poinar, G. O., *J Invert Pathol* (1973) 22:228-230). An additional report that Neoaplectana desiccate in nature under unspecified conditions appears in a symposium abstract (Kamionek, M. et al, "Eleventh Int'l Symp Nematol. Eur Soc Nematol" (1972)).

Other types of nematodes, including free living and plant parasitic nematodes, are known to survive naturally under dry conditions (Evans, A.A.A.F. et al, in "Nematodes as Biological Models" (1980) Academic Press, New York, pp. 193-211; Demeure, Y. et al, in "Plant Parasitic Nematodes" (1981) Academic Press, New York). It has been shown that significant changes in chemical composition occur in preparation for the anhydrobiosis caused by desiccation, and it is known that the plant parasitic nematodes which form the subjects of these studies, must be preconditioned at 97-98% relative humidity for 48-72 hours before being subjected to lower relative humidity (Evans et al (supra); Womersley, C., *Comp Biochem Physiol* (1981) 68A:2-49-252; Madin, K.A.C., et al. *J Expl Zool* (1975) 143:335-342; Crowe, J. H., et al, (ibid) 323-334).

Freckman, D. W. et al, in "New Trends in Soil Biology" (Lebrun, P. ed.) (1983) Universities Catholique de Louvain Press, discuss the ability of nematodes in desert soils to survive anhydrobiosis. Womersley, C. *Compar Biochem Physiol* (1981) 70B: 669-678 reviews the mechanisms of anhydrobiotic survival in nematodes; similar studies are reported by Crowe, J. H., et al. *J Exp Zool* (1979) 207:431-437; Demeure, Y., et al. *J Nematol* (1979) 11:189-195 and Crowe, J. H., et al, *Ann Meet Amer Inst Biol Sci*, East Lansing, Mich. 21-26 August 1977.

However, with respect to species of interest in insect control, the one report of an attempt to desiccate *N. carpocapsae* (Simons, W. R., and Poinar, G. O., supra) utilized a series of humidity chambers containing glycerol solutions. Relative humidity (RH) was not measured directly, nor was the temperature at which the experiment was conducted reported. IJs were held at 96% RH for 12 hr, transferred to 93% for a further 12 hr, and then to RHs ranging from 10-79% for periods up to 28 days. Only at 79.5% RH was survival greater than 40% after 12 days; even under these conditions viability fell to 30% after 20 days.

The present invention is based on the findings that 1) a minimum period for induction of anhydrobiosis at high RH is required and that 2) Steinernematid and Heterorhabditid infective juveniles are extremely fastidious with respect to accurate and constant RH control. The latter point has relevance with respect to acceptable means for carrying out the invention and with regard to the interpretation of the literature. In particular, we have found that when glycerol is used to control RH, nematode survival after induction of anhydrobiosis is highly variable. Nematode survival data after induction of anhydrobiosis in air whose RH is controlled by sulfuric acid solutions, on the other hand, is highly consistent. We have directly measured the RH levels above glycerol solutions and found them to be unreliable and unpredictable for the precise control required. Far more consistent RH control is achieved with sulfuric acid solutions. Thus, the results of Simons and Poinar are difficult to interpret because glycerol does not offer a dependable means to control RH.

In short, none of the published studies of nematode desiccation provide guidance for effecting anhydrobiosis in Steinernematid and Heterorhabditid entomogenous nematodes in a scalable process to ensure effective, commercially practical, long-term mass storage and shipment.

DISCLOSURE OF THE INVENTION

The invention provides processes for placing Steinernematid and Heterorhabditid nematode infective juveniles into a state of anhydrobiosis, thus facilitating long-term mass storage while maintaining their viability and pathogenicity over long periods of storage and during shipment. The invention also provides containers suitable for maintaining nematodes in this anhydrobiotic condition, and convenient for effecting the rehydration of the infective juveniles at the site of use, and, of course, the invention provides the anhydrobiotic nematodes per se. The methods and materials provided by the invention are significant in enabling the economically sound and commercially viable use of Steinernematid and Heterorhabditid nematodes for insect control in agricultural applications. Absent such methods and materials, high cost packaging and refrigeration would have to be used, or the infective juveniles would have to be cultivated very close to the site of application rendering this approach to pest control for the most part impractical, and resulting in the continued use of chemical insecticides some of which have been shown to be ecologically harmful.

Therefore, in one aspect, the invention is directed to a process for inducing an anhydrobiotic state in Steinernematid and Heterorhabditid nematodes, which comprises causing the evaporation of the bulk of the surface moisture from a thin layer of a high density IJ nematode suspension, followed immediately by subjecting the IJs to a relative humidity (RH) of 95-99% for at least two days, thus inducing the anhydrobiotic state, and then, optionally, reducing the relative humidity to 50-94% for an indefinite period of storage. The anhydrobiotic nematodes may also be maintained at the inducing RH of 95-99%.

In another aspect, the invention is directed to the anhydrobiotic IJs obtained by the method of the invention.

In other aspects, the invention relates to containers useful in shipping and/or storage of the IJs which have been thus placed in an anhydrobiotic or cryptobiotic state. The containers of the invention are characterized by their capacity to control the relative humidity experienced by the contained nematodes and to provide sufficient oxygen to supply minimal metabolic requirements in the low level of metabolism characterizing this state. Thus, in one embodiment the containers are impermeable to moisture, preferably insulated, the relevant interiors are nontoxic to nematodes, and there is sufficient headspace to meet the oxygen requirements of the cyptobiotic IJs. A typical such container has a lid or other sealing device which is sealed during storage, but removable to permit the removal of the IJs for use.

In another embodiment, the container is permeable to water and air, but has at least two compartments separated by a nonwettable or hydrophobic barrier which permits the movement of water vapor between the compartments. One compartment is used to house the desiccated nematodes, the other to contain means to maintain the appropriate relative humidity. For example, a saturated salt solution whose vapor pressure provides the correct value for relative humidity may be used. There is sufficient exchange with the surrounding atmosphere through the membrane or other material comprising the container to supply the minimal oxygen requirements of the stored IJs.

In still another aspect, the invention relates to aggregates of entomogenous infective juveniles in a state of apparent cryptobiosis.

MODES OF CARRYING OUT THE INVENTION

A. Definitions

Figure 1:
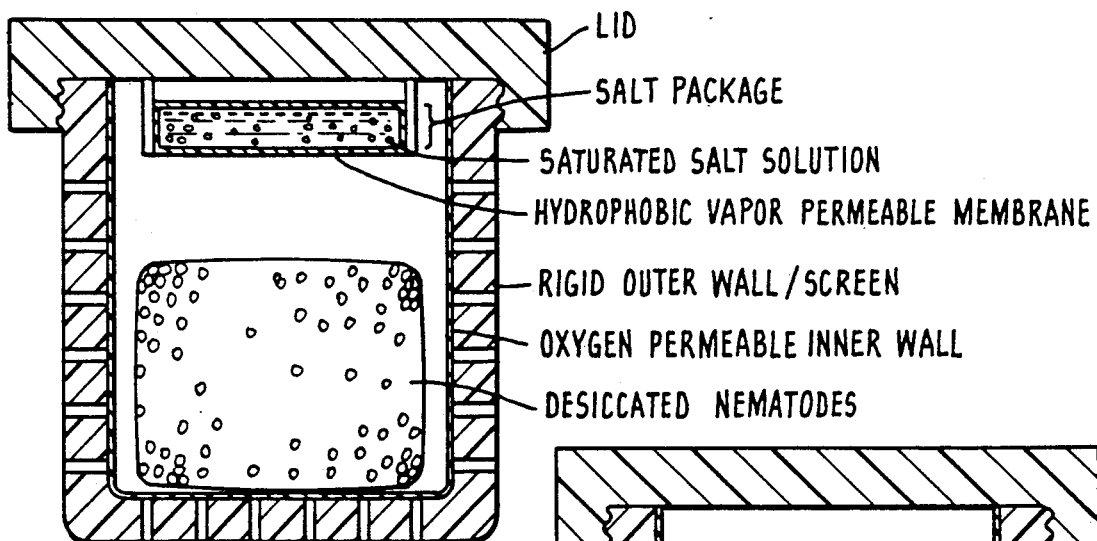
FIG. 1-4 show representative alternative containers of the invention suitable for storage and shipment of desiccated infective juveniles.

"Entomogenous nematodes" refers to nematodes which are parasitic to one or more species of insect. The most important Order of entomogenous nematodes is the Rhabditida, and the invention is directed chiefly to storage and/or shipment of two Rhabditid families in this group: the Steinernematidae and the Heterorhabditidae. However, other entomogenous families may also be suitable as subjects to which the methods of the invention may be applied, and include Diplogasteridae, Panagrolaimidae, Rhabditidae, and Syrophonematidae, together with non-Rhabditid families including the Allantonematidae, Aphelenchoididae, Entaphelenchidae, Mermithidae, Neotylenchidae, Sphaerulariidae, and Tetradonematidae.

As set forth above, for the Rhabditida, the most important families for commercial use are the Steinernematidae and the Heterorhabditidae. References in the literature to "Neoaplectana" refer to a particular genus of the Steinernematidae, and the terms Neoaplactana and Steinernema as designators for specific species—e.g., *N. glaseri* or *S. glaseri*—are sometimes used interchangeably.

While the classification of the various groups of nematodes may be confusing, it is clear that the invention is directed to those genera which have the characteristics of being infective to insects, and which have as a stage in their life cycles, stage 3 infective juveniles (IJs) with the characteristics described in the background section above. Depending on the agricultural application intended, i.e., the insect targeted, one or more of the species may be particularly advantageous.

"Network of high specific surface area" refers to an arrangement assumed by the IJ nematodes during surface water loss which maximizes exposure of the nematode surface to the air.

"Cryptobiotic state" refers, in the context of the present invention, specifically to a cryptobiotic state of the infective juvenile. It is a reversible physiological state of dormancy in which metabolism is suppressed. If measures of relative insensitivity are employed to ascertain metabolism, the metabolism may, in fact, go undetected. In this state, oxygen uptake is greatly reduced and may be undetectable using certain conventional means for relatively short times.

"Anhydrobiosis" refers to a cryptobiotic state induced by evaporative water loss. "Apparent anhydrobiosis" or "apparent cyptobiosis" refers to such a state as determined by the following criteria: lack of movement, shrunken and shriveled appearance, and reduced oxygen consumption. (The apparently anhydrobiotic or cyptobiotic nematodes can be shown still viable by rehydrating them and testing for viability and pathogenicity.)

In particular, the anhydrobiotic or cyptobiotic state of the IJs of the invention can be evidenced by any of the following criteria:

(1) In a population of at least 1,000 infective juveniles, more than 60% can successfully be rehydrated and found viable after being suspended in 70% methanol wherein the suspension is then plunged into liquid nitrogen for 24 hours and thereafter rapidly thawed to room temperature.

(2) In a population of at least 1,000 infective juveniles, more than 70% survive maintenance in an airtight container at a nematode/volume ratio of $10^6/30$ ml, wherein air occupies the volume of the container initially. The maintenance time is temperature dependent. The required percentage can be maintained for more than 15 days at 25° C., for more than 8 days at 30° C., or for more than 6 days at 35° C.

(3) In an aggregation of more than 1,000 IJs, with no free liquid water present, the oxygen demand is less than 1 ml oxygen per 80 mg dry weight of IJs per day at 25° C. The contrast with nonanhydrobiotic nematodes can easily be seen, in that for "normal" nematodes, the oxygen demand would be in excess of 6 ml of oxygen per $10^6$ organisms.

(4) In a population of at least 1,000 IJs, more than 90% survive exposure to 45° C. for 2 hours.

"Desiccated nematodes" also refers to nematodes in an apparent anhydrobiotic state.

"Infective juvenile" or "IJ" refers to a nonadult stage capable of invading and infecting an insect host. For the families which are the subject of the present invention, these are stage 3 IJs.

"Relative humidity" ("RH") is defined in a standard manner as the ratio of water vapor pressure in the air to the saturation vapor pressure at the same temperature, and is normally expressed as a percent.

B. General Description

The infective juveniles which are the subjects of the procedures herein are useful in controlling a variety of insect pests, including borers, root weevils, caterpillars, beetle grubs, corn root worms, Japanese beetles, and mole crickets. Major agricultural products which are protected by such infective juveniles include corn, strawberries, almonds, greenhouse crops, mushrooms, sugar cane, and potatoes. Poultry raising facilities and other animal housing, also, are kept free of flies. In a typical agricultural application, infective juveniles are applied to the target environment in large numbers. For example, for control of sciarid flies in mushroom houses, approximately $5 \times 10^9$ worms are sprayed in each house. Smaller numbers of IJs, e.g., about $10^6$, might be useful for home applications; this number would be suitable for protection of a single potted plant.

Using present technology, approximately $10^{11}$ infective juveniles, or about 25 kg of wet product, can be grown per week in about 152 kg of culture medium. These large numbers of IJs must be preserved, shipped, and stored.

In the process of the present invention, large numbers of IJs are maintained for long periods for these purposes in a anhydrobiotic state using evaporative desiccation. The effect of this process is to result in IJs which retain their viability and pathogenicity.

Viability is determined by microscopic observation wherein the criteria for viable individuals include: a transparent esophogeal region, the absence of the typical death position, and motility when rolled with a dental probe.

Pathogenicity is determined by assaying the infective juveniles against *Galleria mellonella* larvae. The infective juveniles in concentrations of 50 per assay dish are pipetted in 0.5 ml water onto a single Whatman No. 1 filter placed in the lid of a 45 mm petri dish. Ten insect larvae are placed on the filter, and the dish is closed and placed at 22° C. and 80% relative humidity. Mortality is recorded at daily 2-hr intervals between 30 and 50 hr post-exposure, and the time required to effect 50% mortality ($LT_{50}$) is compared to controls.

Surface Water Removal

The process of the invention has two essential steps: surface water removal, followed by induction of anhydrobiosis. In general, surface water removal is effected by harvesting the infective juveniles, washing or resuspending in water, and re-harvesting a high density layer of the organisms with a high surface area.

In a typical procedure, an aqueous suspension of IJs at known concentration of, for example, $5 \times 10^5$/ml is vacuum filtered to a high-density layer 1-4 mm thick. The bulk of the surface water is then evaporated off, during which process a characteristic network of high specific area is formed. It is important to ascertain that the subject nematodes have been freed of surface moisture, and to subject them immediately to induction conditions described below, so that desiccation does not proceed too rapidly. On the other hand, if surface moisture remains, anhydrobiosis will not occur during induction.

Assessment of complete surface water removal can be made by determination of the weight (mass) of the high density layer per organism. As would be expected, the expected weight per $10^6$ nematodes of the resulting "dry" worms varies with the particular species, and is proportional to size. For example, for *N. carpocapsae* evaporation of surface water is complete when the determined weight is about 0.2 g/$10^6$ worms, for example, between about 0.18 and 0.21 grams, and for *H. heliothidis* the corresponding weight is about 0.16 g/$10^6$ worms, for example, between about 0.13 and 0.17 grams. Other species will have characteristic masses of their own; for example, *N. glaseri* and *N. bibionis*, are expected to result in masses of approximately 0.4 g/$10^6$ IJs.

Induction of Anhydrobiosis

Immediately after the initial evaporation of surface moisture, the IJs are subjected to environmental conditions of $97 \pm 2\%$ RH and a temperature range of 12°-35° C., much more preferably 20°-25° C., for a period sufficient to effect apparent anhydrobiosis, i.e., to "induce" this condition. This period seems to be a minimum of two days, but extended times may also be used. The time required will vary depending on the precise conditions, and the species of worm used but will be at least approximately two days.

The relative humidity must be kept within the prescribed range during this period, and any convenient means effective in doing this may be used. It should be noted that for Steinernematid and Heterorhabditid nematodes, precise RH generation and maintenance are essential for successful induction of anhydrobiosis and subsequent revival of the nematodes. It appears that the use of glycerol solutions, as disclosed in the art, is not satisfactory. Two convenient acceptable methods are as follows.

In one alternative, following removal of the bulk of the surface water, the nematode network of high specific surface area is placed in a chamber, such as a desiccator, wherein the relative humidity is controlled by sulfuric acid/water mixtures of the appropriate concentration (Groves, D. W. et al, *J Soc Chem Indust* (1940) 59:175-177; Solomon, M. E., *Bull Ent Res* (1951) 42:543-554). If desired, this method can also be used for control of RH over long periods of subsequent storage, but is, of course, not appropriate for a commercial scale.

In another alternative, especially suitable for commercially useful IJ volumes in excess of $5 \times 10^8$ worms, nonstatic processes are preferred. Environmental chambers through which air of preconditioned humidity is circulated are then preferred. Various means of such preconditioning are known in the art, including but not limited to saturation of air by a vapor spray at low temperature followed by heating to the set point. As stated above, the temperature at which the set point should the reached is optimally in the range of 20°-25° C., and the relative humidity must be controlled to $97 \pm 2\%$ for the temperature selected. Any other means of achieving dependable and effective control of RH are also usable in the process of the invention.

Storage

After the induction period, the nematodes may be kept in the inducing RH range, but further reduction in RH may be convenient. Thus, following the above induction period, the nematodes may, if desired, be maintained at lower relative humidities in the range of 50-94%, preferably 70-94%, and most preferably 85-94%, or they can continue to be stored at 95-99% RH.

Besides correct maintenance of the relative humidity in a suitable range, provision must be made for sufficient oxygen supply to accommodate the low level of metabolism of the IJs in their anhydrobiotic/cryptobiotic state. It was originally thought that the oxygen demand of the IJs in this state was zero; however, this finding was subsequently shown to be attributable to relatively insensitive measuring techniques or short measuring time. When ascertained by more sensitive methods, it is demonstrable that IJs in this state require on the order of 0.6-1 ml of oxygen per 80 mg dry weight per day at 25° C. The manner of storage must be designed so as to provide this amount of available oxygen.

The oxygen demand has been referenced against weight, based on a tested species in which 80 mg of IJs corresponds to approximately $10^6$ organisms (*N. carpocapsae*). For other species, the relative amount of oxygen per organism will vary according to the size of the organism, while the weight per mg of IJs remains relatively constant across the entomogenous species.

For the storage containers to provide adequate oxygen in a small package, the packaging can be made of semipermeable materials which allow the passage of oxygen, as long as provision is also made for maintenance of the correct relative humidity. For example, a saturated solution of potassium sulfate will maintain a 97% relative humidity, and this solution could be incorporated in a gel matrix, e.g., a hydrogel such as Terasorb, or can be placed in a fibrous matrix, e.g., cellulose or other fiber. The humidity-maintaining composition is preferably separated physically from the stored nematodes in the container, and the separation may be effected by a non-wettable, moisture permeable barrier.

An alternative embodiment is an airtight (and moisture-tight) container with sufficient air space to accommodate the needs of the stored IJs for the desired time period. In this embodiment, maintenance of correct RH is automatic; no special precautions need by taken. This is practical for smaller numbers of nematodes, but may be troublesome if large numbers, e.g., $10^9$, of nematodes are desired to be stored over long time periods since considerable volume is required. The amount of head space can be calculated on the basis of the value of the oxygen requirement, as set forth above.

Rehydration

After the period of storage, the anhydrobiotic nematodes IJs must be rehydrated for use. Upon rehydration, the anhydrobiotic state is lost, and the IJs regain their metabolic activity. Viability and pathogenicity can be confirmed as described above. Two general approaches to rehydration are appropriate: direct and "slow".

For direct rehydration, the desiccated IJs are simply placed in water or an isotonic aqueous solution, or the compartment containing the IJ preparation is filled with water or an isotonic solution. After 2-3 hr of rehydration, the IJs are rehydrated and may be tested for viability/pathogenicity. They should preferably be used within 24 hours of rehydration.

In some cases, rehydration may advantageously be less abrupt. For such "slow" rehydration, which is particularly advantageous when Heterorhabditids are used, the worms are placed in controlled environments a preliminary period, such as in 100% RH air or relatively high osmotic pressure solutions for 20 hr. Appropriate solutions may contain 2.5% NaCl or 10% myoinositol, for example. After this period of acclimation, the nematodes are immersed in water and directly rehydrated as described above.

Containers

The container used for storage and/or shipment may be of a variety of convenient designs. Its essential characteristic is that it must maintain the remaining water content of the IJs, generally by maintaining the correct RH at a constant level and must provide the minimal $O_2$ demand of the desiccated IJs. Of course, the components of the container in contact with the desiccated nematodes must be nontoxic to them. In addition, the entire container is preferably insulated or otherwise regulated with regard to controlling temperature change.

In one examplary embodiment, the container provides separate compartments, one for an RH maintaining means, such as an appropriate solution, and one for the desiccated IJs. These compartments are separated by a non-wettable barrier which permits passive bidirectional passage of water vapor. Examples of suitable hydrophobic materials include Gortex or porous Teflon membranes. The desiccated nematodes may be in the form of loosely stacked or rolled layers, pellets (2-20 mm diameter), or a packed mass. The compartment housing the desiccated nematodes is constructed of an oxygen-permeable material so that oxygen demand can be supplied. The volume of the solution which maintains the relative humidity must be sufficient to maintain the RH of the package against water loss despite the oxygen permeability required for the maintenance of the nematodes. Thus, an adequate volume of the RH-maintaining solution must be provided commensurate with the desired shelf life of the container. A number of configurations are illustrated below for the juxtaposition of the relevant compartments.

Figure 2:
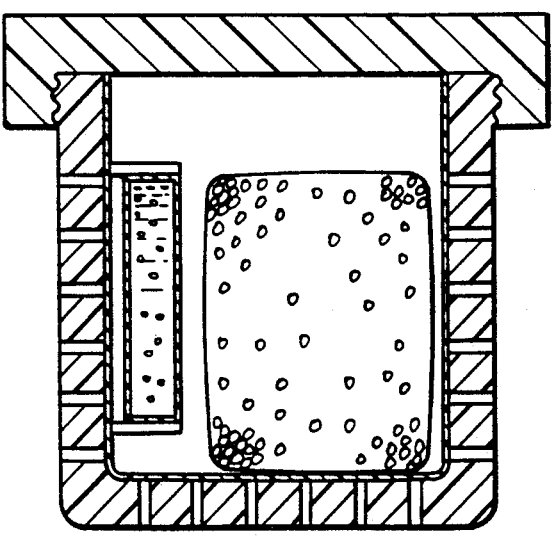
Figure 3:
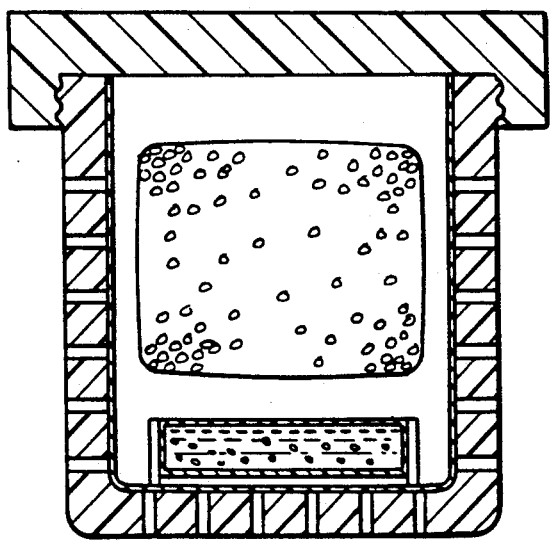

Illustrated in FIG. 1 are variants of a "two-compartment" package. This is a crushproof container with a lid which can be a simple screw cap or clamped-on plate. On the inside of the lid (FIG. 1), or positioned elsewhere in the container (FIGS. 2-3), is a package of saturated salt solution separated from the remainder of the container by a hydrophobic material which allows bidirectional passage of water vapor. As shown, the position of the RH-maintaining compartment is not critical—it may reside at the side of the container, at the bottom, or it may remain free within the container. The container is $O_2$ permeable to the extent needed to meet the $O_2$ demand. For example, the nematode package is thus permeable and the outer supporting walls may be screens or porous, of sufficiently small pore size that the RH can be maintained.

Figure 4:
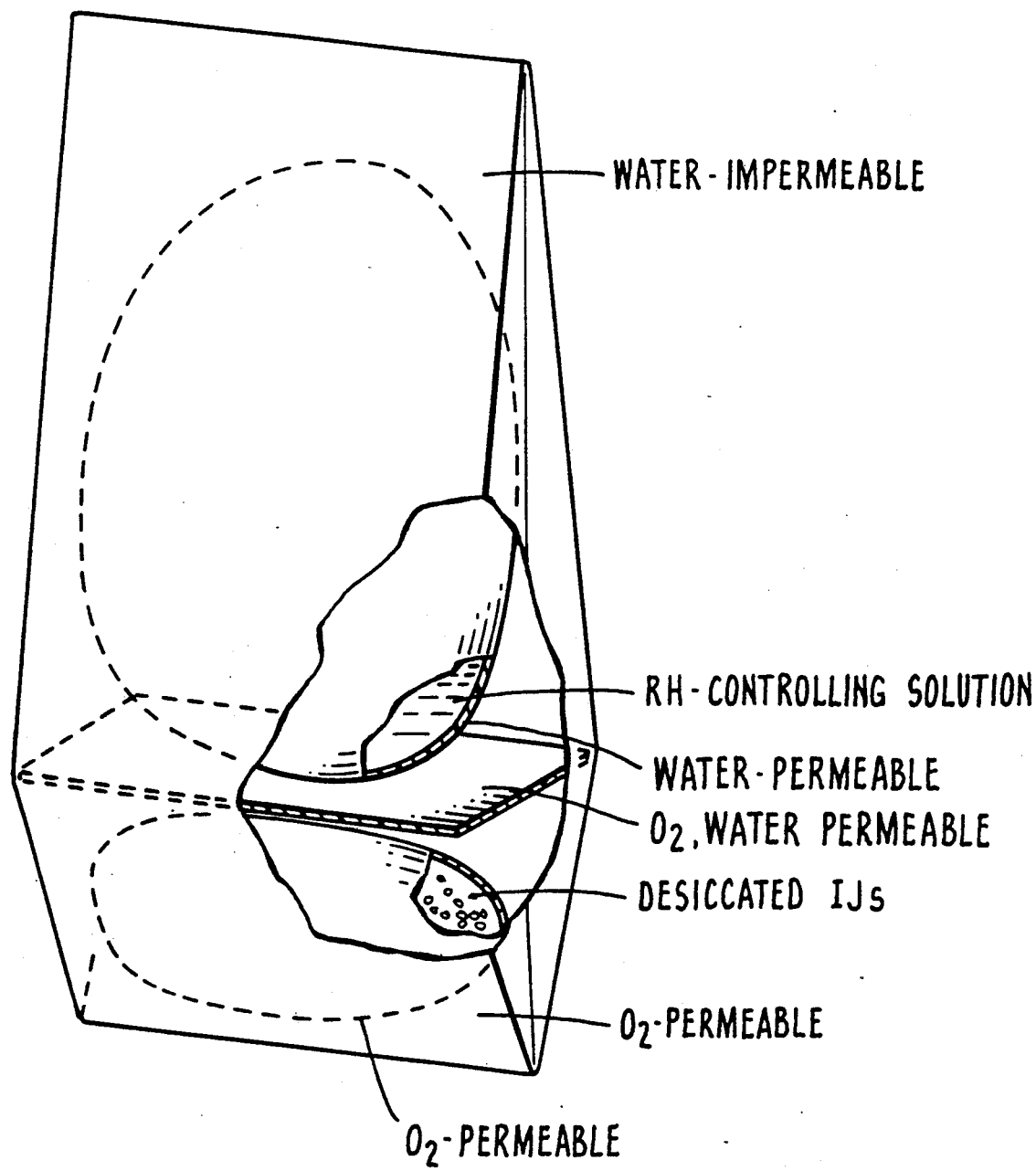

In another alternative, the container may comprise a flexible material which is sealed upon itself (FIG. 4). In this embodiment, the flexible container includes the desired separate compartments described above, and is sealed. It can be opened with scissors.

An alternative, but less preferred, form of packaging is a tightly sealed container without the inclusion of a device which maintains RH. The air space surrounding or above the desiccated nematodes should therefore be adequate to provide the required oxygen.

It is preferable to perform the packaging of desiccated nematodes in these containers in an environment whose RH is that at which the desiccated nematodes are best stored. The package may also contain a crystalline salt, or an alternative compound which when dissolved in water for rehydration enhances survival. This material may be optionally included with the desiccated IJs or provided separately, so that the design of the container facilitates slow rehydration at the appropriate time in situ.

EXAMPLES

The following examples are illustrative but not limiting of the invention.

PREPARATION A

Preparation of Infective Juveniles

*N. carpocapsae* or other entomogenous species are grown under standard culture conditions and infective juveniles obtained as described by Bedding, R. A., *Ann Appl Biol* (1984) 104:117-120.

EXAMPLE 1

Desiccation of *Neoaplectana carpocapsae*

A water suspension of in vitro derived IJs of *N. carpocapsae* as described in Preparation A was vacuum filtered onto filter discs to give $10^7$ IJs per disc ($=2.5\times10^6$ IJs per square inch). Surface water was allowed to evaporate from the IJ layers at 22° C. and 50% RH until the nematodes on each disc weighed 2 g (0.2 g/$10^6$ IJs) and the IJs assumed a network of high specific surface area.

Nalgene polycarbonate desiccators (volume=1300 cc) containing 100 ml of 10% (w/w) sulfuric acid (=97% RH-Solomon, M. E., *Bull Ent Res* (19) 42: 543-554) were prepared in advance and equilibrated at 25° C. An RH of 97% inside the desiccators was confirmed with a Beckman RH sensor (Humi-check 5).

Three filter discs of IJs were placed on the shelf of each desiccator and the desiccator lids quickly replaced. The desiccators were maintained at 25° C. and 97% RH for 3 days.

The filters were then transferred to desiccators containing 100 ml of a saturated solution of potassium chloride (=85% RH-Greenspan, L., *J Res Nat Bur Stds* (19) 81A: 89–96). Three IJ samples per test point were periodically removed and rehydrated by direct immersion in water. After 24 h the nematodes were tested for viability and pathogenicity as described above. Table 1 shows the results.

TABLE 1

Viability and pathogenicity of IJs of *N. carpocapsae* after storage at 85% RH and 25° C.

| Time (months) | % Viability (mean of 3 trials) | Pathogenicity (% with respect to freshly harvested IJs) |
|---|---|---|
| 1 | >95 | 100 |
| 2 | >95 | 100 |
| 3 | >95 | 100 |
| 4 | >95 | 100 |
| 5 | >95 | 100 |

Subsequent determinations using these conditions gave slightly less positive results.

EXAMPLE 2

Desiccation of *N. bibionis*

A water suspension of in vitro derived IJs of *N. bibionis* as described in Preparation A was vacuum filtered onto filter discs to give $10^7$ IJs per disc (=$1.5 \times 10^6$ IJs per square inch). Surface water was allowed to evaporate at 22° C. and 50% RH until the nematodes on each disc weighed 4.0 g (0.4 g/$10^6$ IJs) and the IJs assumed a network of high specific surface area.

Nalgene polycarbonate desiccators containing 100 ml of 10% (w/w) sulfuric acid (=97% RH) were prepared in advance and equilibrated at 25° C. An RH of 97% inside the desiccators was confirmed with a Beckman RH sensor.

Three filter discs of IJs were placed on the shelf of each desiccator and the desiccator lids quickly replaced. The desiccators were maintained at 25° C. and 97% RH for 3 days. A sample was withdrawn, rehydrated, and found to be viable.

The filters were divided into four groups and stored at the following conditions: 97% RH at 4° C. or 25° C. and 94% RH at 4° C. or 25° C. (94% RH was maintained using a saturated potassium nitrate solution.) Three samples per test point were withdrawn periodically and tested for pathogenicity and viability. Over a period of three months all samples from all four conditions showed viability of >95% and pathogenicity of 100% as compared to freshly harvested IJs.

EXAMPLE 3

Desiccation of *Heterorhabditis heliothidis*

A water suspension of in vitro derived IJs of *H. heliothidis* prepared as in Preparation A was vacuum filtered onto filter discs to give $10^7$ IJs per disc (=3.5 IJs per square inch). Surface water was allowed to evaporate at 22° C. and 50% RH until the nematodes on each disc weighed 1.6 g (0.16 g/$10^6$ IJs), and the IJs assumed a network of high specific surface area.

Nalgene polycarbonate desiccators containing 100 ml of 10% (w/w) sulfuric acid (=97% RH) were prepared in advance and equilibrated at 25° C. 97% RH inside the desiccators was confirmed with a Beckman RH sensor.

Three discs of IJs were placed on the shelf of each desiccator and the desiccator lids quickly replaced. The desiccators were maintained at 25° C. and 97% RH for 3 days. A sample of nematodes was then rehydrated and found to be >95% viable.

Some filters were further maintained at 97% RH, others were transferred to desiccators containing 100 ml of a saturated solution of potassium nitrate (=94% RH). IJ samples stored at 97% RH were periodically removed and directly rehydrated by direct immersion in water.

IJ samples which had been stored at 94% for 2 months were either rehydrated directly or slowly rehydrated by subjecting them to:

a) 100% RH for 20 h, or b) incubation in 2.5% sodium chloride for 20 h, or c) incubation in 10% myoinositol for 20 h, prior to immersion in water. After 24 h in water, the IJs were tested for viability and pathogenicity. Table 2 shows the results. All determinations are the mean of 3 samples per test point. All samples tested showed 100% pathogenicity.

TABLE 2

Viability of IJs of *H. heliothidis* after storage at 25° C. and 97% or 94% RH

| Time (months) | | % Viability (mean of 3 trials) | |
|---|---|---|---|
| 97% RH storage | | | |
| 1 | | >95 | |
| 2 | | >95 | |
| 3 | | >95 | |
| | | Slow rehydration Method | |
| 94% RH storage | Direct rehydration | a | b | c |
| 1 | 65 | — | | |
| 2 | 65 | 93 | 89 | 93 |
| 3 | 50 | 90 | 91 | 94 |

EXAMPLE 4

Determination of Optimal Storage Temperature for *N. carpocapsae*

Aliquots of $10^7$ IJs of *N. carpocapsae* were vacuum filtered and prepared for induction of anhydrobiosis as described in Example 1.

Filter discs each supporting $10^7$ IJs were maintained in desiccators at 97% RH and 25° C. as described in Example 1.

Desiccators containing 100 ml of a 17.9% (w/w) solution of sulfuric acid (=90% RH) were prepared in advance and equilibrated at the following temperatures: −10, 6, 10, 20, 25, 35, and 40° C.

Three filter discs of IJs were placed on each shelf of the desiccators and maintained at 90% RH over the aforementioned temperature range. IJ samples (3 per test point) were periodically removed and rehydrated by direct immersion in water. After 24 hr the nematodes were tested for viability and pathogenicity. Table 3 shows these results as % viability (mean of 3 trials).

TABLE 3

Viability of IJs of *N. carpocapsae* stored at 85% RH

| Temp. (°C.) | Time (days after induction) | | | | | | | |
|---|---|---|---|---|---|---|---|---|
| | 8 | 21 | 35 | 49 | 64 | 75 | 89 | 132 |
| 40 | 0 | 0 | 0 | 0 | 0 | 0 | 0 | 0 |
| 35 | 95 | 99 | 57 | 0 | 0 | 0 | 0 | 0 |
| 25 | 98 | 97 | 99 | 98 | 98 | 99 | 98 | 98* |
| 20 | 99 | 98 | 97 | 94 | 98 | 98 | 98 | 98* |
| 10 | 98 | 99 | 96 | 96 | 98 | 98 | 99 | 98* |
| 6 | 97 | 99 | 94 | 94 | 97 | 98 | 98 | 98* |
| −10 | 92 | 76 | 74 | 64 | 3 | 0 | 0 | 0 |

*IJs were as pathogenic as freshly harvested IJs.

EXAMPLE 5

Determination of Optimal Storage Temperature for *H. heliothidis*

Aliquots of $10^7$ IJs of *H. heliothidis* were vacuum filtered and induced into anhydrobiosis as described in Example 3.

Filters were maintained at 97% RH or 94% RH at various temperatures, and samples (3 per test point) withdrawn at various intervals. The samples were rehydrated directly or by slow hydration in 2.5% NaCl for 20 hours before immersion in water. Table 4 shows the results as % viability.

TABLE 4

Viability of IJs of *H. heliothidis* stored at 97% and 94% RH and a range of temperatures

| 97% RH Temp. °C. | Time (months after induction) | | |
|---|---|---|---|
| | 1 | 2 | 3 |
| 40 | 0 | — | — |
| 35 | 71 | 0 | — |
| 25 | >95 | >95 | >95* |
| 20 | >95 | >95 | >95* |
| 10 | >95 | >95 | >95* |
| 6 | >95 | >95 | >95* |
| −10 | 35 | 0 | >95* |
| −10 | 35 | 0 | — |

| 94% RH | 1 | | 2 | | 3 | |
|---|---|---|---|---|---|---|
| | Direct rehydr. | Slow rehydr. | Direct rehydr. | Slow rehydr. | Direct rehydr. | Slow rehydr. |
| 40 | 0 | — | — | — | — | — |
| 35 | 60 | 0 | 0 | 0 | — | — |
| 25 | 65 | — | 65 | 90 | 49 | 89* |
| 20 | 60 | — | 55 | 92 | 56 | 93* |
| 10 | 68 | — | 64 | 94 | 60 | 94* |
| 6 | 69 | — | 69 | 91 | 63 | 93* |
| −10 | 10 | — | 0 | 0 | — | — |

*IJs were as pathogenic as freshly harvested IJs

As shown in Table 4, viability is maintained at 97% RH over a period of three months at temperatures of 6°-25° C. Viability abruptly diminishes at higher or lower temperatures. At 94% RH, a similar temperature optimum is obtained.

EXAMPLE 6

Requirement for Surface water removal—*N. carpocapsae*

A water suspension of in vitro derived IJs of *N. carpocapsae* was vacuum filtered onto filter discs to give $10^7$ IJs per sample. Surface water was allowed to evaporate from the IJ layers under conditions of 22° C. and 50% RH until the weights per $10^6$ IJs ranged from 0.13-0.31 g. IJ samples were then placed in desiccators at 97% RH and 25° C. for 3 days. The samples were again weighed, and apparent anhydrobiosis determined. Samples (3 per test point) exhibiting anhydrobiosis were placed in desiccators at 90% RH and 25° C. for 3 days, and then rehydrated by direct immersion in water (24 hr) and tested for viability. Table 5 shows these results.

TABLE 5

Effect of Pellet Weight on Survival

| After Evaporation | Weight per $10^6$ (g) after Induction | After 3 days at 90% | Viability after 3 days at 90% RH (%) |
|---|---|---|---|
| 0.130 | 0.160 | 0.140 | 0[1] |
| 0.197 | 0.168 | 0.146 | 96 |
| 0.203 | 0.164 | 0.136 | 92 |
| 0.216 | 0.163 | 0.138 | 95 |
| 0.310 | 0.263[2] | — | — |

[1] IJs could not tolerate the extreme preliminary evaporation which led to water gain during induction.
[2] IJs still moving—i.e., not desiccated.

These results make clear that if more than surface moisture is directly removed, the IJs do not survive. On the other hand, failure to remove surface moisture results in failure to achieve desiccation.

EXAMPLE 7

Requirement for Surface water removal—*H. heliothidis*

A water suspension of in vitro derived IJs of *H. heliothidis* was vacuum filtered onto filter discs to give $10^7$ IJs per sample. Surface water was allowed to evaporate from the IJ layers under conditions of 22° C. and 50% RH until the weights per $10^6$ IJs ranged from 0.146-0.2 g. IJ samples were then placed in desiccators at 97% RH and 25° C. for 3 days. The samples were again weighed, and apparent anhydrobiosis determined. Samples exhibiting anhydrobiosis were placed in desiccators at 97% RH and 25° C. for 3 days, and then rehydrated by direct immersion in water (24 hr) and tested for viability. Table 6 shows these results.

TABLE 6

Effect of Pellet Weight on Survival

| After Evaporation | Weight Per $10^6$ (g) after Induction | % Viability after 3 days at 97% RH |
|---|---|---|
| 0.146 | 0.140 | 0[1] |
| 0.154 | 0.142 | 95 |
| 0.158 | 0.140 | 95 |
| 0.168 | 0.144 | 95 |
| 0.172 | 0.146 | 95 |
| 0.200 | 0.170[2] | — |

[1] IJs could not tolerate the extreme preliminary evaporation which led to water gain during induction.
[2] IJs still moving—i.e., not desiccated.

These results also make clear that if more than surface moisture is directly removed, the IJs do not survivee. On the other hand, failure to remove surface moisture results in failure to achieve desiccation.

EXAMPLE 8

Large Scale Desiccation of *Neoaplectana carpocapsae*

A 20 cu. ft. environmental chamber (Model CL5632 Parameter Generation and Control Inc.) was set to be conditioned with air at 25° C. and 97% RH by a 500 cfm conditioner running at 250 cfm. The air flow in the chamber was transverse. A 180 cu ft environmental walk-in room (PGC) was set to be conditioned at 25° C. and 97% RH by a 500 cfm conditioner running at 500 cfm. The air flow within the room was from a diffuser in the ceiling to a return diffuser at the base of a side wall.

The PGC method of parameter generation works as follows: air returning from the chamber/room enters a spray chamber and is saturated with water at a predetermined temperature, such that when the air is heated to the set-point temperature, the required RH is achieved. This is a simple and reliable system which does not rely on a feedback mechanism.

Aliquots of $10^6$ IJs in suspension were vacuum filtered onto filter discs. Surface water was allowed to evaporate from the IJ pellets for 10 min under the conditions of 20° C. and 60% RH. During this time the IJs assumed the configuration of a network of high specific area.

IJ pellets were placed at each corner and in the center of each of 5 shelves in the chamber and on each end of 4 shelves spaced from the floor to 6 ft. high on either side of the room. To simulate loading of the chamber or room, trays containing water-soaked filter paper were placed on the rest of the shelf space. Both chamber and room were left to run for 3 days.

After 3 days all of the IJ pellets has desiccated. Most of the desiccated IJ pellets were rehydrated directly in water. IJs from all samples revived within an hour and were >95% viable. Some of the desiccated pellets which had been situated nearest to the incoming air flow and nearest to the return plenum/diffuser in both chamber and room were placed in storage containers in which 90% RH was controlled by a saturated solution of potassium nitrate contained within a sealed Goretex bag. The containers of desiccated IJs were stored under ambient temperatures ranging from 15°-30° C. for 5 days and then rehydrated directly to water. IJs from all samples revived within 2 hr were >95% viable and as pathogenic as freshly harvested controls.

EXAMPLE 9

Effect of Inadequate Relative Humidity Control

A 33 cu. ft. environmental chamber (Hotpack, Inc.) was set to be conditioned with air at 25° C. and 97% RH. The air flow within the room was from top to bottom.

The Hotpack method of parameter generation works as follows: a wet/dry bulb sensor in the chamber senses air and wet bulb temperature. The sensor feeds back to the control system and steam is put into the air, which has already been heated to the set-point temperature, such that the set-point RH is achieved.

*N. carpocapsae* IJ samples, prepared as in Example 8, were placed at each corner and in the middle of each of 9 shelves and the chamber examined. None of the samples had desiccated, and 40 out of the 50 IJ pelles had become wet with condensation. Water had condensed on all surfaces within the chamber.

It was concluded that the above method of chamber conditioning is unable to provide the specific RH conditions required for successful induction of anhydrobiosis.

EXAMPLE 10

Storage in Containers with Controlled RH

Filter discs containing $10^6$ *N. carpocapsae* and *H. heliothidis* were prepared and induced into anhydrobiosis as described in Examples 1 and 3 respectively.

Gortex bags having 2 in$^2$ surface area were filled with 2 ml of saturated potassium sulfate (97% RH).

The prepared IJs were placed in 300 ml Freund Can Co tins along with the appropriate RH Gortex bags and the lids sealed. The cans were stored at 4° C. or 25° C. Samples were directly rehydrated and tested for viability and pathogenicity.

Over a period of two months, all samples showed viability of >95% and pathogenicity of 100%. Thus, both species of infective juvenile maintained infectivity at either temperature for at least two months under the RH conditions tested.

EXAMPLE 11

Lack of High Oxygen Requirement in Anhydrobiotic IJs of *N. carpocapsae* and *H. heliothidis*

IJs of *N. carpocapsae* and *H. heliothidis* were desiccated for 3 days at 97% RH and 25° C. according to the methods described in Examples 1 and 3.

Desiccated IJs of both species and freshly harvested non-desiccated IJs were suspended in 2M sucrose immediately before being injected into the chamber of an YSI $O_2$ monitor. The temperature was maintained at 25° C. by circulating water from a constant temperature water bath through a water jacket around the chamber. $O_2$ uptake was recorded for 10 minutes per sample and the nematodes were then removed and resuspended in water. Viability was determined 2 h later. Table 7 shows the $O_2$ consumption results for both desiccated and freshly harvested IJs.

TABLE 7

| Effect of Desiccation on $O_2$ Consumption and Viability $O_2$ uptake (mmol $O_2/10^6$ IJs/min) | | |
|---|---|---|
| | Freshly harvested IJs | Desiccated IJs |
| *N. carpocapsae* | $2.5 \times 10^{-4}$* | 0* |
| *H. heliothidis* | $1.6 \times 10^{-4}$* | 0* |

*IJs were >95% viable following resuspension in water for 2 h.

As shown in the examples below, the foregoing results, leading to the conclusion that desiccated IJs do not require oxygen, resulted from the short time periods used for measurement. When more sensitive tests are employed, a reduced, but measurable $O_2$ demand is found.

EXAMPLE 12

Oxygen Demand of Desiccated *N. carpocapsae*

Discs of $2 \times 10^6$ IJs of *N. carpocapsae* were induced to anhydrobiosis over 3 days at 97% RH and 25° C. according to the method described in Example 1. Discs were then individually transferred to 60 ml vials sealed air tight with butyl rubber sampling septa. The vials were maintained at temperatures ranging from 5°-40° C. (Some vials were gassed with 2% $O_2$ in $N_2$ and maintained at 25° C.) Vials containing $2 \times 10^6$ non-desiccated IJs were also maintained at 25° C. as controls. Headspace gas samples were periodically taken using a locking gas sampling syringe and $O_2$ concentration was determined with a Mocon $O_2$ analyzer. The results are shown in Table 8.

TABLE 8

| Temperature (°C.) | Oxygen uptake rate (ml $O_2/10^6$ IJs/day) |
|---|---|
| 5 | 0.15 |
| 10 | 0.23 |
| 20 | 0.31 |
| 25 | 0.61 |
| 30 | 0.80 |
| 35 | 1.23 |

TABLE 8-continued

| Temperature (°C.) | Oxygen uptake rate (ml $O_2/10^6$ IJs/day) |
| --- | --- |
| 40 | 1.53 |

As indicated in Table 8, the oxygen demand increases with temperature. It also appears to increase with the concentration of oxygen present as a 2% oxygen atmosphere at 25° C. shows an oxygen demand reduced to 0.20 ml $O_2/10^6$ IJs per day, as compared to the 0.62 ml $O_2$ required by $10^6$ nematodes maintained at the same temperature in air at approximately 20% oxygen. By comparison, a control sample of non-desiccated *N. carpocapsae* IJs had an oxygen requirement of 7.5 ml/$10^6$ IJs per day at 25° C.

The values determined in Table 8 permit the calculation of the volume of head space required at various temperatures for a desired time of shelf life. For example, Table 9 shows the results for $10^6$ IJs of the calculations for 20° C. and 30° C. and varying self lives. The volume required is, of course, directly proportional to the shelf life desired.

TABLE 9

| Temperature (°C.) | Shelf Life (days) | Volume (ml) |
| --- | --- | --- |
| 20 | 30 | 45 |
|  | 60 | 90 |
|  | 90 | 135 |
| 30 | 30 | 120 |
|  | 60 | 240 |
|  | 90 | 360 |

EXAMPLE 13

Calculation of Packaging Parameters

Because, as shown in Example 12, the volumes required for reasonable shelf life are fairly substantial if the container is air tight, design parameters have been determined for containers which are permeable to oxygen, and thus also for water. These containers require a means to maintain the desired RH. The results in Table 10 are required oxygen transfer rates calculated in ml oxygen per package per day for $10^7$ desiccated *N. carpocapsae* IJs at various temperatures.

TABLE 10

| Storage Temperature (°C.) | Required Oxygen Transfer Rate (ml $O_2$/package day) |
| --- | --- |
| 20 | 3.0 |
| 25 | 5.5 |
| 30 | 8.0 |
| 35 | 20.0 |

Three materials were then used as the basis for the determination of packaging parameters: low density polyethylene (LDPE), fluorinated ethylene propylene copolymer (FEP), and a polyethylene rubber obtained from Allied Chemical Company (Pax 3303). Based on the known oxygen permeability of each of these materials, a required surface area was calculated. From this area, the amount of moisture transiting the membrane permits calculation of the required volume of RH-maintaining solution required to maintain the relative humidity. The results of these calculations, shown in Table 11, were based on a film thickness of 1 mil and a shelf life of 1 year.

TABLE 11

| Material | Storage Temperature (°C.) | Package Surface Area (in²) | Reservoir Volume (ml) |
| --- | --- | --- | --- |
| LDPE | 25 | 6 | 23 |
| FEP (Teflorx) | 25 | 3.5 | 5 |
| Polyethylene rubber (Pax 3303) | 25 | 3.9 | 18 |
| LDPE | 20 | 3.3 | 12.5 |
| FEP (Teflorx) | 20 | 2.0 | 2.8 |
| Polyethylene rubber (Pax 3303) | 20 | 2.1 | 9.8 |
| LDPE | 30 | 8.8 | 33 |
| FEP (Teflorx) | 30 | 5.3 | 7.5 |
| Polyethylene rubber (Pax 3303) | 30 | 5.6 | 26 |

Of course, variations in the containers can be made to accommodate changing temperatures, as is calculable from the results of the temperature change. Alternatively, the package may also contain head space to accommodate temporary increases in temperature. For example, an LDPE package designed for 20° C. would provide sufficient oxygen subjected to 30° C. for 6 hours, if it included a head space of 7 ml. A similar package made of FEP would require 4 ml head space (based on $10^7$ IJs per package).

EXAMPLE 14

Demonstration of Enhanced Liquid Nitrogen Freezing Survival of Desiccated IJs of *N. carpocapsae*

Pellets (100,000 IJs/pellet) of *N. carpocapsae* were desiccated as described in Example 1 for periods up to 72 hours. At 24, 48, and 72 hours, pellets were dropped into a solution of 70% methanol which had been precooled on ice. The nematode suspensions were periodically agitated for 10 min and then aliquoted in 20 μl drops onto precooled glass slivers. The glass slivers were plunged into liquid nitrogen. Non-desiccated IJs were frozen according to the same procedure. Following 24 hours of freezing, the glass slivers were removed from the liquid nitrogen and dropped into a vial of room temperature saline which was immediately agitated for 1 minute. Nematode survival was determined after 6 hours of maintenance in the saline. The results are shown in Table 12.

TABLE 12

| Time at 97% Relative Humidity (hours) | Freezing Survival (%) |
| --- | --- |
| 0 | 8 |
| 24 | 82 |
| 48 | 80 |
| 72 | 82 |

EXAMPLE 15

Survival of Desiccated and Non-Desiccated IJs of *N. carpocapsae* in Air Tight Containers IJs of *N. carpocapsae* were filtered onto filter discs ($2 \times 10^6$/disc). One group was desiccated according to the procedure described in Example 1. Discs of desiccated and non-desiccated IJs were transferred to 60 ml airtight vials and maintained at 25° C. On a daily basis vials were opened and the nematodes were washed out with water. Viability of the non-desiccated nematodes was determined immediately. The desiccated nematodes were allowed to rehydrate overnight and then viability was determined. The results are shown in Table 13.

TABLE 13

| Time (days) | Viability (%) | | | | | |
|---|---|---|---|---|---|---|
| | Desiccated | | | Non-Desiccated | | |
| | 25° | 30° | 35° | 25° | 30° | 35° |
| 1 | 95 | 93 | 93 | 95 | — | — |
| 2 | 95 | — | 90 | 95 | — | — |
| 3 | 95 | — | — | 95 | — | — |
| 4 | 95 | 93 | 85 | 95 | — | — |
| 5 | 95 | — | — | 95 | — | — |
| 6 | 95 | — | — | 95 | — | — |
| 7 | 95 | 91 | 80 | 95 | — | — |
| 8 | 95 | 90 | — | 95 | — | — |
| 9 | 95 | 25 | — | 95 | — | — |
| 10 | 95 | — | — | 95 | — | — |
| 11 | 95 | — | — | 95 | — | — |
| 12 | 95 | — | — | 95 | — | — |
| 13 | 95 | — | — | 95 | — | — |
| 14 | 95 | — | — | 60 | — | — |
| 15 | 95 | — | — | 38 | — | — |
| 16 | 95 | — | — | 20 | — | — |
| 17 | — | — | — | — | — | — |

EXAMPLE 16

Survival of Desiccated and Non-Desiccated IJs of *N. carpocapsae* Exposed to 45° C.

IJs of *N. carpocapsae* were filtered onto filter discs. One group of discs were desiccated according to the procedure described in Example 1. Segments of discs were individually placed in screw-cap vials and maintained at 45° C. Periodically samples were removed, suspended in water, and nematode viability was determined 24 hours later. The results are shown in Table 14.

TABLE 14

| Time (hours) | Viability (%) | |
|---|---|---|
| | Desiccated | Non-Desiccated |
| 0 | 96 | 98 |
| 2 | 94 | 78 |
| 4 | 91 | 8 |

We claim:

1. A process for placing entomogenous nematode infective juveniles selected from the group consisting of *N. carpocapsae*, *N. bibionis*, and *H. heliothidis* in an anhydrobiotic state which process comprises:
   (a) substantially removing bulk surface moisture from said infective juveniles; and
   (b) inducing anhydrobiosis in said infective juveniles by exposure to air at a relative humidity of 97±2% for a period sufficient to achieve anhydrobiosis as defined by one or more of the following survival characteristics wherein:
      (i) more than 60% survive when said nematodes are suspended in 20% methanol, said methanol is cooled to liquid nitrogen temperature for 24 hours, and said suspension is rapidly brought to room temperature;
      (ii) more than 90% survive when maintained in an airtight container at a nematode/volume ratio of $10^6/30$ ml of air atmosphere for
         (1) 10 days at 25° C., or
         (2) 8 days at 30° C., or
         (3) 6 days at 35° C.;
      (iii) said infective juveniles require less than 1 ml oxygen per 80 mg dry weight nematodes per day at 25° C. in the absence of external moisture; or
      (iv) more than 90% of said infective juveniles survive exposure to air at 45° C. for 2 hr.

2. A process for storage of entomogenous nematode infective juveniles selected from the group consisting of *N. carpocapsae*, *N. bibionis*, and *H. heliothidis* in an anhydrobiotic state which process comprises conducting the process of claim 1 followed by storing the IJs resulting from step (b) under conditions selected from the group consisting of
   (a) ambient RH of 50–94%;
   (b) ambient RH of 70–94%;
   (c) ambient RH of 85–94%; and
   (d) ambient RH of 95–99%.

3. Anhydrobiotic nematodes prepared by the process of claim 1.

4. A composition consisting essentially of a biologically pure preparation of at least 1,000 entomogenous nematode infective juveniles selected from the group consisting of *N. carpocapsae*, *N. bibionis*, and *H. heliothidis* prepared by the process of claim 1 from a culture thereof, said infective juveniles having an anhydrobiotic metabolic state as defined by the survival characteristic wherein more than 90% of said infective juveniles survive exposure to air at 45° C. for 2 hr.

* * * * *